US010102623B2

(12) United States Patent
Kido et al.

(10) Patent No.: US 10,102,623 B2
(45) Date of Patent: Oct. 16, 2018

(54) COMPUTER PROGRAM, AND IMAGE PROCESSING DEVICE AND METHOD

(71) Applicants:Fujifilm RI Pharma Co., Ltd., Chuo-ku (JP); National University Corporation Ehime University, Matsuyama-shi (JP)

(72) Inventors: Teruhito Kido, Toon (JP); Yuki Tanabe, Toon (JP); Hikaru Nishiyama, Toon (JP); Teruhito Mochizuki, Toon (JP); Kenya Murase, Suita (JP); Tsutomu Souma, Chuo-ku (JP)

(73) Assignees: Fujifilm RI Pharma Co., Ltd., Tokyo (JP); National University Corporation Ehime University, Ehime (JP)

( * ) Notice: Subject to any disclaimer, the term of this patent is extended or adjusted under 35 U.S.C. 154(b) by 0 days.

(21) Appl. No.: 15/326,398

(22) PCT Filed: Jul. 10, 2015

(86) PCT No.: PCT/JP2015/069865
§ 371 (c)(1),
(2) Date: Jan. 13, 2017

(87) PCT Pub. No.: WO2016/009957
PCT Pub. Date: Jan. 21, 2016

(65) Prior Publication Data
US 2017/0206652 A1 Jul. 20, 2017

(30) Foreign Application Priority Data

Jul. 15, 2014 (JP) ................................ 2014-144794

(51) Int. Cl.
*G06T 7/00* (2017.01)
*A61B 6/03* (2006.01)
(Continued)

(52) U.S. Cl.
CPC .......... *G06T 7/0012* (2013.01); *A61B 5/0402* (2013.01); *A61B 6/03* (2013.01);
(Continued)

(58) Field of Classification Search
USPC .................................................. 382/128–134
See application file for complete search history.

(56) References Cited

U.S. PATENT DOCUMENTS

| 2002/0172408 | A1* | 11/2002 | Saito ...................... A61B 6/032 |
| | | | 382/132 |
| 2003/0040669 | A1* | 2/2003 | Grass ................... A61B 6/4014 |
| | | | 600/407 |
| 2007/0126730 | A1* | 6/2007 | Goto .................. A61B 5/02007 |
| | | | 345/418 |

FOREIGN PATENT DOCUMENTS

| JP | 2003116843 | 4/2003 |
| JP | 2007151881 | 6/2007 |

(Continued)

OTHER PUBLICATIONS

"International Application No. PCT/JP2015/069865, International Search Report and Written Opinion dated Oct. 6, 2015", (dated Oct. 6, 2015), 9 pgs.

(Continued)

*Primary Examiner* — Alex Liew
(74) *Attorney, Agent, or Firm* — Schwegman Lundberg & Woessner, P.A.

(57) ABSTRACT

An analysis method is provided that ensures objective and quantitative analysis for analyzing time-series images. For implementing the method are provided an image data storage unit that stores therein image data on a plurality of time-series computed tomography (CT) images of an organ of a subject captured after a contrast medium has been administered; a target pixel extraction unit configured to extract an intra-organ pixel position, which is a position of (Continued)

a pixel in a region of the organ; a change-over-time determining unit configured to determine a change-over-time of a CT value of the pixel at the determined intra-organ pixel position, based on image data on the time series CT images in the plurality of frames; and a function approximation processing unit configured to determine an arrival time at which the contrast medium has arrived at an organ at the intra-organ pixel position and a base value, which is a CT value serving as a base of the pixel at the intra-organ pixel position, based on the determined change-over-time.

16 Claims, 8 Drawing Sheets

(51) Int. Cl.
    *G06T 7/11*     (2017.01)
    *A61B 5/0402*     (2006.01)
    *A61B 6/00*     (2006.01)

(52) U.S. Cl.
    CPC .............. *A61B 6/032* (2013.01); *A61B 6/481* (2013.01); *A61B 6/503* (2013.01); *A61B 6/504* (2013.01); *A61B 6/5211* (2013.01); *G06T 7/11* (2017.01); *G06T 2207/10081* (2013.01); *G06T 2207/30048* (2013.01); *G06T 2207/30104* (2013.01)

(56) References Cited

FOREIGN PATENT DOCUMENTS

| JP | 2009028065 | 2/2009 |
| JP | 2011083437 | 4/2011 |
| JP | 2011152187 | 8/2011 |
| JP | 2012161444 | 8/2012 |
| WO | WO-2012153539 | 11/2012 |
| WO | WO-2013156901 | 10/2013 |
| WO | WO-2016009957 | 1/2016 |

OTHER PUBLICATIONS

Cheong, L. H., et al., "An automatic approach for estimating bolus arrival time in dynamic contrast MRI using piecewise continuous regression models", Phys. Med. Biol. 48 (2003) N83-N88, (Feb. 18, 2003), N83-N88.

"European Application No. 15821307.4, Extended European Search Report dated Feb. 20, 2018", (dated Feb. 20, 2018), 48 pgs.

\* cited by examiner

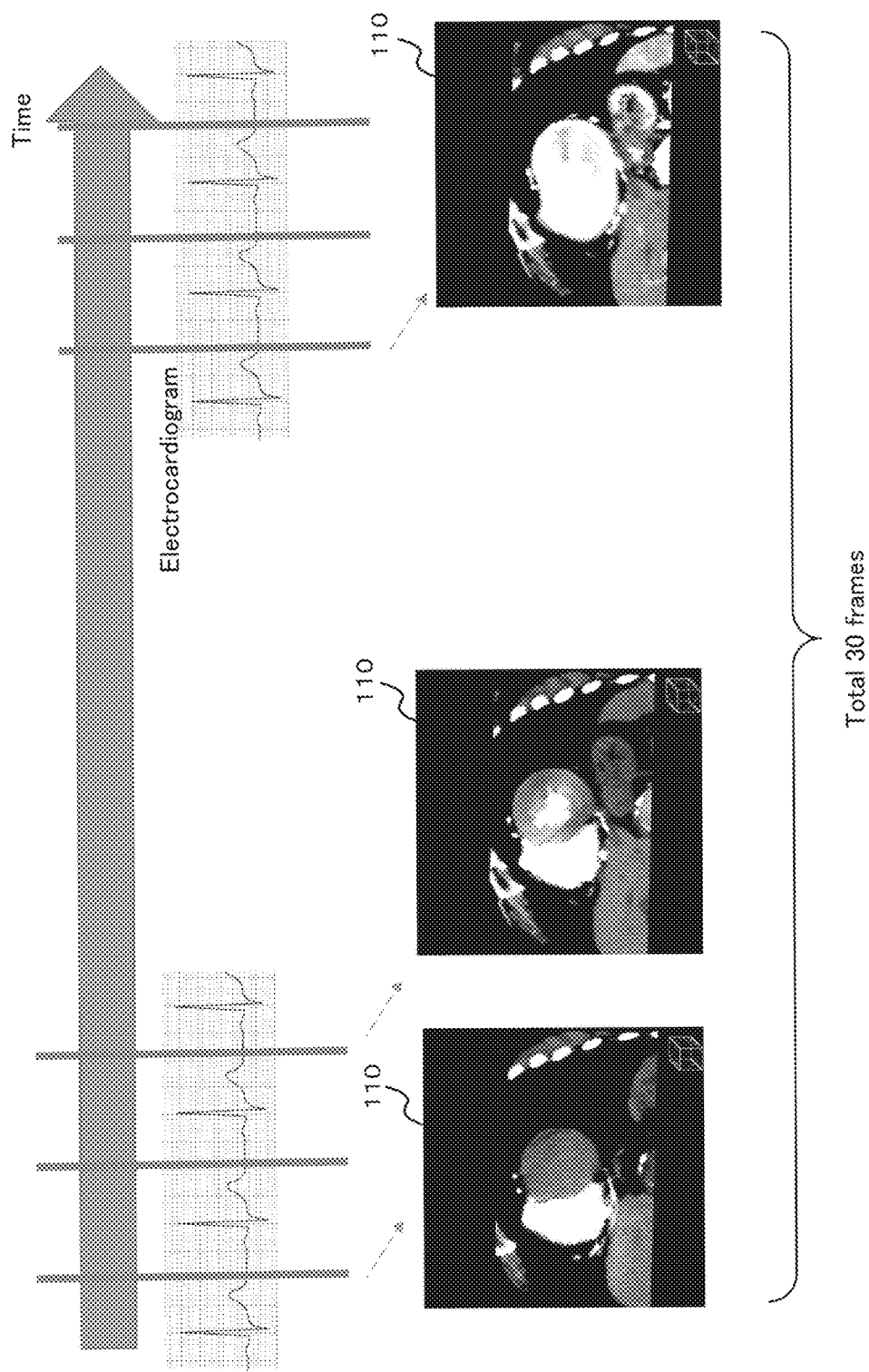

Input function table 130

| Arrival time | Base value | Functions L and F | ROI Value |
|---|---|---|---|
| 23 | 45 | ... | ... |

Output function table 150

| Slice No | Pixel position | Arrival time | Base value | Functions L and F | Sampling value |
|---|---|---|---|---|---|
| 1 | x1,y1 | 5 | 22 | ... | ... |
| 1 | x2,y2 | 6 | 25 | ... | ... |
| ... | ... | ... | ... | ... | ... |

COMPUTER PROGRAM, AND IMAGE PROCESSING DEVICE AND METHOD

PRIORITY CLAIM TO RELATED APPLICATIONS

This application is a U.S. national stage application filed under 35 U.S.C. § 371 from International Application Serial No. PCT/JP2015/069865, which was filed 10 Jul. 2015, and published as WO2016/009957 on 21 Jan. 2016, and which claims priority to Japanese Application No. 2014-144794, filed 15 Jul. 2014, which applications and publication are incorporated by reference as if reproduced herein and made a part hereof in their entirety, and the benefit of priority of each of which is claimed herein.

TECHNICAL FIELD

The present invention relates to an image processing technique, and particularly relates to a technique of analyzing time-series dynamic images.

BACKGROUND ART

A known method for analyzing a blood flow in the heart uses images of the heart of a subject captured after a contrast medium has been administered to the subject.

Single photon emission computed tomography (SPECT) is a myocardium perfusion inspection that has been widely employed in medical practices for some time. The SPECT inspection has advantages in that it involves less contraindications, it is a well-established inspection method, and whole heart imaging is employed. Sufficient evidence has been found for further advantages of the SPECT inspection. More specifically, an incidence of cardiac events can be estimated in accordance with severity of myocardium ischemia detected by the SPECT inspection. In this context, a best outcome can be achieved by selecting a treatment policy in accordance with the severity. However, the SPECT inspection has disadvantages in that spatial resolution is insufficient, and it cannot be executed concurrently with coronary stenosis assessment.

Recently, there have been many reports on effectiveness of a magnetic resonance imaging (MRI) inspection for myocardium ischemia assessment. The MRI inspection has advantages such as no radiation exposure, less side effects from a contrast medium, and a high spatial resolution. Still, the MRI inspection has disadvantages such as long inspection time, variations in heart phases due to difference in a data collection time phase between slices, and contraindication such as pacemakers unsuitable for the MRI.

A stress myocardium perfusion computed tomography (CT) is a noninvasive stress myocardium perfusion inspection that has recently been reported to be effective. The inspection has a huge advantage over other modalities in that it can assess whether the subject suffers from myocardium ischemia, with coronary CT angiography concurrently conducted through highly accurate coronary artery morphology assessment. Up until recently, perfusion CT has mainly relied on single shot-examination involving imaging only in a single time phase under stress, and qualitative assessment has been performed on a static image. Actually, the imaging timing optimum for the myocardium perfusion assessment differs between cases, and it has been difficult to capture an image while measuring an imaging timing. Fortunately, recent development of imaging devices has enabled a quantitative assessment on the myocardium perfusion through analysis on a time density curve (TDC) obtained by a dynamic scan.

NPL 1 discusses a method of analyzing the TDC. The method includes: analyzing a time-series dynamic MRI images of the heart; and calculating an arrival time indicating a time at which a contrast medium has arrived at a predetermined myocardium region.

In clinical point of view, advancement of CT devices has led to remarkable improvement in spatial and temporal resolution in coronary CT inspections for the heart. Thus, the coronary CT inspection is widely used for medical diagnostics of circulatory organs, as a noninvasive inspection with the same diagnostic accuracy with coronary angiography (CAG). Furthermore, development of CT devices such as a plane detector CT, a high-resolution CT, and a dual-surface CT has made way for new image techniques such as subtraction imaging and dual energy imaging used in clinical practice. Thus, now the coronary CT inspection may be effective for the coronary stenosis assessment in cases deemed to have been difficult such as hyperdynamic, arrhythmia, and coronary artery calcification cases.

It has been widely known that even when a symptom of morphological coronary stenosis has been found, it does not necessarily mean that a symptom of functional myocardium ischemia has been found. Whether coronary stenosis lesion involves myocardium ischemia is an important factor for determining whether to perform revascularization treatment (such as catheter therapy or surgical therapy, for example). Unfortunately, in actual practice, whether to conduct therapeutic intervention on the coronary stenosis lesion, found by the coronary CT inspection, may be determined based on uncertain symptoms in some cases. More specifically, there might not be enough time or enough medical staff to perform a plurality of different inspections (the coronary stenosis assessment and the myocardium ischemia assessment) before the therapeutic intervention is conducted. This is because ischemic heart diseases are peculiar in that delay in the therapeutic intervention could be critical.

CITATION LIST

Patent Literature

[NPL 1]
An automatic approach for estimating bolus arrival time in dynamic contrast MRI using piecewise continuous regression models Phys. Mde, Biol. 48(2003) N83-N88

SUMMARY OF INVENTION

Technical Problem

In the prior art technique described above, a region of interest (ROI) is set in a myocardium region by an analyst such as a physician. The arrival time indicating an arrival at the myocardium region is determined based on a pixel value in the ROI. Appropriate setting of the ROI highly depends on the experience and skill of the analyst. The conventional method involves manual setting of the ROI for analysis that could be biased by a subjective view of an observer. The ROI-based analysis yields a result of analyzing only the pixels in the ROI, and thus might lead to an ambiguous result with normal and abnormal regions mixed and averaged. All things considered, the conventional method is likely to involve differences among analysts meaning that objectivity is lost.

For the analysis on the time-series dynamic images of the heart, an objective and more detailed pixel analysis without manual setting of the ROI by the analyst has been called for.

In view of the above, an object of the present invention is to provide an objective and quantitative analysis method for analyzing time-series images.

Another object of the present invention is to provide a more detailed analysis method for analyzing the time-series images of the heart.

Still another object of the present invention is to provide an inspection method with which coronary stenosis assessment and coronary artery assessment can be accurately performed in a short period of time.

Solution to Problem

A computer program according to an aspect of the present invention for an image processing device including a storage unit that stores therein image data on time-series computed tomography (CT) images in a plurality of frames, of an organ of a subject captured after a contrast medium has been administered causes the image processing device to execute: determining an intra-organ pixel position, which is a position of a pixel in a region of the organ; determining a change-over-time of a CT value of the pixel at the determined intra-organ pixel position, based on image data on the time series CT images in the plurality of frames; and determining an arrival time at which the contrast medium has arrived at an organ at the intra-organ pixel position and a base value, which is a CT value serving as a base of the pixel at the intra-organ pixel position, based on the determined change-over-time.

In a preferred aspect, the computer program may further cause the image processing device to execute: determining as an upper limit frame a predetermined frame after a sharp rise in the CT value in the determined change-over-time; and approximating the change-over-time before the upper limit frame with two or more functions. The arrival time and the base value may be determined with the two or more approximated functions.

In a preferred aspect, the computer program may further cause the image processing device to execute: determining as an upper limit frame a predetermined frame after a sharp rise in the CT value in the determined change-over-time; and approximating the change-over-time before the upper limit frame with a normal cumulative distribution function or a cumulative distribution function. The arrival time and the base value may be determined with the approximated normal cumulative distribution function or cumulative distribution function.

In a preferred aspect, the computer program may further cause the image processing device to execute approximating the determined change-over-time with an mth-order function (m being a number equal to or larger than three). The upper limit frame may be determined based on the mth-order function obtained by the approximating, and two or more functions may include alinear and a quadratic function approximated to the mth-order function before the upper limit frame.

In a preferred aspect, the computer program may further cause the image processing device to execute setting a region of interest (ROI) including a plurality of pixels in a blood vessel region through which blood flows into the organ. The change-over-time of the CT value may be a change-over-time in an ROI value determined based on a CT value of the pixel in the ROI set in the setting. The arrival time may be an arrival time at which the contrast medium has arrived at the blood vessel region determined based on a change-over-time in the determined ROI value. The base value may be determined based on the CT value of the pixel in the blood vessel region.

In a preferred aspect, in the determining the intra-organ pixel position, a pixel with a CT value within a predetermined range may be selected in all the time-series CT images in the plurality of frames.

In a preferred aspect, in the determining the pixel position, the pixel position may be selected based on a difference between a maximum value and a minimum value of the CT value in the plurality of time-series CT images.

In a preferred aspect, the organ may be a heart, and the times-series CT images in the plurality of frames may be CT images captured in synchronization with an electrocardiogram.

BRIEF DESCRIPTION OF DRAWINGS

FIG. 2 is diagram illustrating a computed tomography (CT) image.

FIG. 4 is a diagram illustrating an example of data structures of an input function table 130 and an output function table 150.

DESCRIPTION OF EMBODIMENTS

An image processing device according to an embodiment of the present invention is described below with reference to the drawings.

Figure 1:
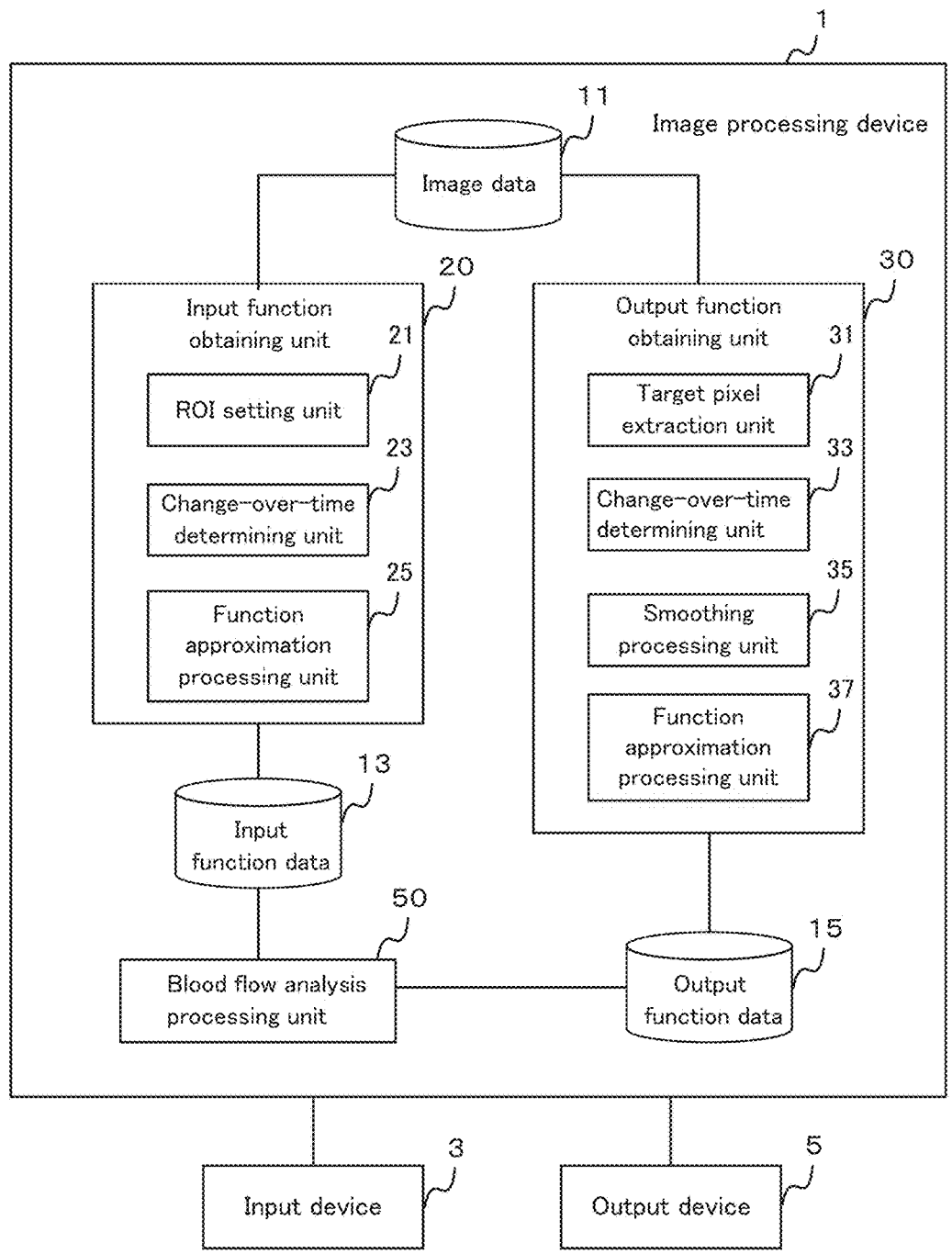
FIG. 1 is a diagram illustrating an overall configuration of an image processing device 1 according to an embodiment of the present invention.

FIG. 1 is a diagram illustrating an overall configuration of an image processing device 1 according to the present embodiment. The image processing device 1 uses CT images of an organ of a subject captured after a contrast medium has been administered, to perform quantitative analysis on a blood flow rate in the organ. For example, in the present embodiment, the image processing device 1 may analyze a plurality of CT frame images of the heart of the subject captured in synchronization with electrocardiogram, by using Iopromide (N,N'-bis(2,3-dihydroxypropyl)-2,4,6-triiodo-5-(2-methoxyacetamido)-N-methylisophthalamide) as the contrast medium. Preferably, the image processing device 1 performs pixel-based analysis on the CT image of the heart described above, to calculate an arrival time and a value (hereinafter, referred to as a base value) serving as a baseline that are used for calculating a quantitative value of a myocardium blood flow.

In the present embodiment, the myocardium blood flow rate may be estimated based on a change in a pixel value of the CT image due to the contrast medium administrated in the vein. For example, when the pixel value of the CT image sharply changes in response to the arrival of the contrast medium at a target portion, the base value may be determined as a pixel value before the arrival and the arrival time may be determined as a time at which the change in the pixel value starts. In such a case, for example, the increased amount of the pixel value from the base value after the arrival time should be due to the contrast medium. All things considered, the blood flow rate may be calculated based on the increased amount from the base value.

For example, the image processing device 1 includes a general-purpose information processing device (computer system). For example, components or functions in the image processing device 1 that are described below are each implemented by executing a computer program that may be stored in a computer-readable recording medium.

The image processing device 1 includes an image data storage unit 11, an input function data storage unit 13, an output function data storage unit 15, an input function obtaining unit 20, an output function obtaining unit 30, and a blood flow analysis processing unit 50. An input device 3 and a display device 5 may be connected to the image processing device 1.

The image data storage unit 11 stores therein image data on a CT image. The image data on a CT image may be three-dimensional voxel data. The CT image may be a three-dimensional image including a plurality of slice images (short-axis images). The CT image may include time-series CT images in a plurality of frames, of an organ of the subject captured after the contrast medium has been administered.

FIG. 2 is a diagram illustrating a CT image. The CT image according to the present embodiment may be a predetermined number of (for example, 30) frame images 110 of the heart corresponding to the same phase of the heartbeat, captured in synchronization with the electrocardiogram. A single frame may include a plurality of slice images. More specifically, data on a single frame may include three-dimensional image data. The figure illustrates an example of frame images obtained with a single slice. The CT image may be started to be captured immediately after the contrast medium is administered to the subject. The CT image may include 1st to 30th frames in the captured order.

Referring back to FIG. 1, the input function obtaining unit 20 may obtain an input function based on image data stored in the image data storage unit 11. The input function relates to change in a pixel value of the CT image (hereinafter, referred to as a pixel value or a CT value) due to the contrast medium flowing into an organ (heart) of the subject.

The input function obtaining unit 20 may further include a ROI setting unit 21, a change-over-time determining unit 23, and a function approximation processing unit 25.

The ROI setting unit 21 selects a region for which the input function is to be determined. The ROI setting unit 21 may set the ROI in the CT image in accordance with an operation of an analyst such as a physician. For example, the ROI setting unit 21 reads out image data from the image data storage unit 11, and displays the frame image of a slice including a target region on the display device 5. The ROI may be set in a region of the aorta as a blood vessel through which the blood flows to the heart, or in a lumen region of the heart. Thus, a slice including the region of the aorta or the lumen region of the heart is selected and displayed on the display device 5. Then, the ROI may be set in the image displayed on the display device 5, in accordance with an input from the analyst through the input device 3. The position of the ROI may be that same among all the frames corresponding to the same slice.

The frame image in which the ROI is set may be an image with which the aorta region can be easily visually recognized. The ROI thus set includes a plurality of pixels.

The change-over-time determining unit 23 may determine the change-over-time in the CT value in the ROI, based on the image data on the time-series CT images in a plurality of frames. For example, the change-over-time determining unit 23 may generate a time density curve (TDC) of the ROI value based on the CT value in the ROI, as the change-over-time in the CT value in the aorta region in the CT image.

Figure 3B:
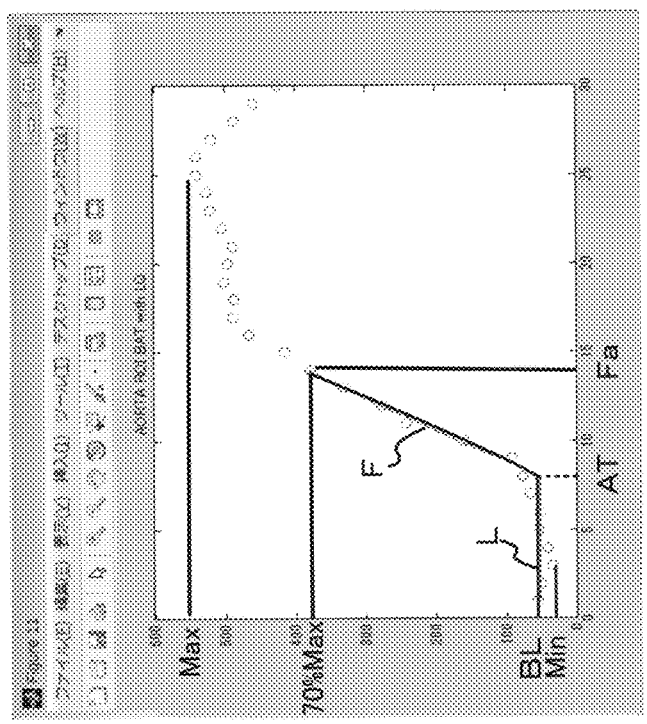
FIG. 3 is a diagram illustrating an example of a time density curve (TDC).
Figure 3A:
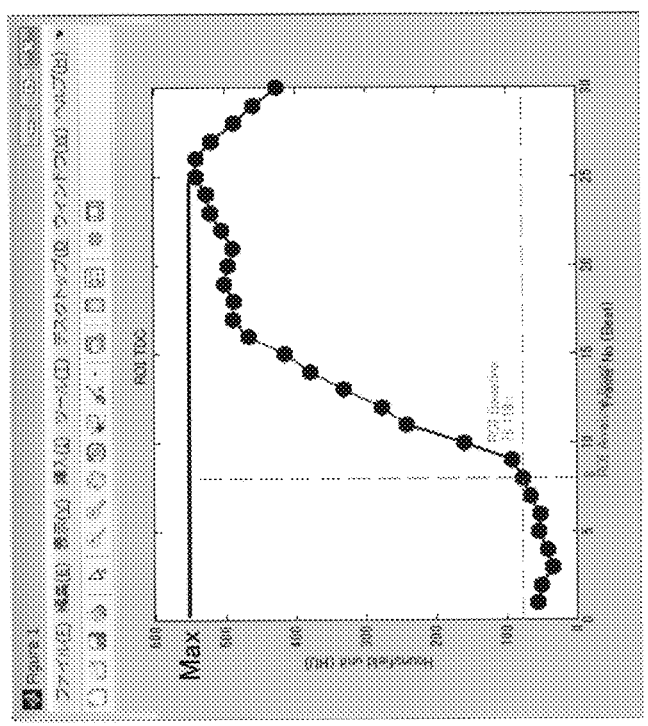

FIG. 3A is a diagram illustrating an example of the TDC. For example, the change-over-time determining unit 23 may apply the ROI set by the ROI setting unit 21 to other frame images 110 corresponding to the same slice. The change-over-time determining unit 23 may determine the ROI value that represents the ROI based on the CT value of the pixels in the ROI for each frame image 110. The TDC illustrated in the figure is generated by plotting the ROI values determined for all the frames corresponding to the same slice. For example, the ROI value is a value (statistical value) as a result of processing the pixel values in the ROI with a statistical algorithm, and may be any of a mean value, a mode value, a median value, a maximum value, a minimum value, and the like.

The change-over-time determining unit 23 may execute smoothing processing to obtain a smooth TDC.

The function approximation processing unit 25 may identify an arrival time at which the contrast medium has arrived at the ROI set as described above, based on the change-over-time in the CT value.

FIG. 3B illustrates ROI values plotted to draw the TDC. Processing of determining the arrival time is described with reference to the figure.

The function approximation processing unit 25 may determine an upper limit frame Fa as a predetermined frame after the sharp rise in the CT value in the change-over-time in the CT value determined by the change-over-time determining unit 23. For example, the upper limit frame Fa may be a single frame before the frame with a peak CT value. The change-over-time determining unit 23 may approximate the TDC before the upper limit frame Fa to a function.

For example, the upper limit frame Fa may be determined as follows. More specifically, the change-over-time determining unit 23 may detect a maximum value Max of the CT value on the TDC or a first peak value after a large rise of the curve (sharp rise in the CT value). Then, the upper limit frame Fa may be a frame that is before a frame from which the maximum value Max or the peak is detected and is of a certain percentage (for example, 70%, 80%, 90%, or the like) between a minimum value Min of the CT values on the TDC and the maximum value Max or the peak value.

The upper limit frame may be determined in a different manner. For example, a rate of change of the TDC may be obtained, and the upper limit frame may be any of frames between the frame with the maximum rate of change and a frame with 0 as the rate of change.

For example, the function approximation processing unit 25 may perform function approximation for the TDC as follows. More specifically, the function approximation processing unit 25 may obtain a formula corresponding a straight line L with a linear approximation method using a least squares method and the like on ROI values before the nth frame Fn (n being any number between 2 and the upper limit frame−1). Similarly, the function approximation processing unit 25 may obtain a formula corresponding to a quadratic function F by approximating to a second order function with the least squares method and the like applied to the ROI values corresponding to frames from the nth frame Fn to the upper limit frame.

The function approximation processing unit 25 may calculate a sum of squares of errors between the straight line L and the ROI values before the nth frame Fn. Similarly, the function approximation processing unit 25 may calculate a sum (residual sum of squares) of squares of errors between the second-order function F and the ROI values at and after the nth frame Fn.

The function approximation processing unit 25 may execute the processing described above for all the n variables, and determine n with the smallest sum of squares of the errors. The function approximation processing unit 25 may determine as an approximated function each of the straight line L and the second-order function F with the smallest error n.

The frame at the intersection (boundary) between the straight line L and the second-order function F may be determined as an arrival time (AT), and the frame at the intersection (boundary) between the straight line L and the second-order function F may be determined as the base value (BL) of the ROI value. Alternatively, for example, the height (Y-intercept) of the straight line L may be used as the base value instead of the ROI value. In this manner, the function approximation processing unit 25 may determine the arrival time and the base value in the aorta region, from the TDC of the ROI value.

In the present embodiment, the function approximation is performed for the TDC with the two functions corresponding to the straight line and the quadratic curve as described above. However, the present invention is not limited to this. For example, the ROI values before the nth frame Fn may be approximated with the straight line L, and the distribution of the ROI values at and after the nth frame Fn may be approximated with a straight line or a higher-order function which is third orders or higher. Alternatively, the distribution of the ROI values in all the frames up to the upper limit frame may be approximated with a function represented by a multidimensional polynomial. In such cases, the arrival time and the base value may be determined in a manner similar to that described above.

Alternatively, the function approximation processing unit 25 may approximate the TDC with three or more functions. For example, the function approximation processing unit 25 may divide the frames from the second frame to the upper limit frame −1 into three sections or more, and may perform approximation in each section with a predetermined function. In the TDC, the CT value might temporarily drop immediately before the curve largely rises (CT value sharply rises). When this happens, the function approximation processing unit 25 may divide the frames into: a section (first section) in which the CT value is almost constant and thus approximation with a straight line can be achieved; a section (second section) in which the CT value drops; and a section (third section) in which the CT value sharply rises thereafter. Then, the function approximation processing unit 25 performs approximation with the straight line in the first section, a function of second order or higher in the second section, and another function of second order or higher in the third section. In such a case, one of the frame at a boundary between the first and the second sections, and the frame at the boundary between the second and the third sections may be determined as the arrival time, and the ROI value of the frame corresponding to the arrival time may be determined as the base value.

The function approximation processing unit 25 may approximate the TDC with a single function. For example, the function approximation processing unit 25 may approximate the TDC with a single function by fitting a normal cumulative distribution function or a cumulative distribution function to the TDC. When function approximation is performed for the TDC with the normal cumulative distribution function, the function approximation processing unit 25 may select a standard deviation (SD) and a mean value of the normal distribution to achieve best fitting to the rising curve of the TDC. For example, in this case, the frame closest to −3 SD of the normal cumulative distribution function approximated to the TDC may be determined as the arrival time and the ROI value of the frame corresponding to the arrival time may be determined as the base value.

The input function data storage unit 13 may store data related to the input function obtained by the input function obtaining unit 20. The input function data storage unit 13 may store therein an input function table 130.

FIG. 4A illustrates an example of a data structure of the input function table 130. As illustrated in the figure, the input function table 130 may include an arrival time 133, a base value 135, functions L and F 137, and an ROI value 139 as data items. The functions L and F 137 may be the straight line L and the second-order function F as a result of approximating by the function approximation processing unit 25 for a frame n=1 to the upper limit frame. The ROI value 139 may be an ROI value of each of frames for forming the TDC. The blood flow analysis processing unit 50 may use the input function for blood flow analysis, with the ROI value 139 or the functions L and F 137 corrected in such a manner that the arrival time 133 and the base value 135 are set to be at the origin.

Referring back to FIG. 1, the output function obtaining unit 30 may obtain an output function representing a change in the pixel value (CT value) of the CT image due to the contrast medium flowing into the blood vessel of the organ (heart) of the subject. In the present embodiment, the output function obtaining unit 30 may obtain the output function for pixels instead of ROIs.

The output function obtaining unit 30 includes a target pixel extraction unit 31, a change-over-time determining unit 33, a smoothing processing unit 35, and a function approximation processing unit 37.

The target pixel extraction unit 31 may extract a pixel for which the output function is obtained, and determine the position of the pixel on the frame image. The pixel to be extracted may be a pixel in the heart region in each slice.

For example, the target pixel extraction unit 31 may execute the following processing for each slice as first extraction processing. More specifically, the target pixel extraction unit 31 may select pixels with the CT value within a predetermined range, in all the time-series CT images in a plurality of frames. For example, the target pixel extraction unit 31 may extract a target pixel as a pixel with the CT value within a range of 30 to 200, in all the frame images corresponding to a single slice.

When the extraction is performed for a heart muscle, the region of the target pixel might include a small non-target region. In such a case, the target pixel extraction unit 31 may regard the region as a processing deficit, and may execute processing of converting the pixel into the target pixel in accordance with the size of the non-target region (for example, whether the number of pixels is a predetermined number or less). When there is an isolated target pixel outside the region of the target pixel, the target pixel extraction unit 31 may execute processing to set the region as the non-target region, in accordance with the size of the isolated target region (for example, whether the number of pixels is a predetermined number or less).

The target pixel extraction unit 31 may execute the following processing on pixels as second extraction processing. More specifically, the target pixel extraction unit 31 may select a pixel based on a changed amount of the CT value of each pixel in the time series CT images in a plurality of frames. An example of the changed amount includes a value representing the difference between the maximum value and the minimum value. For example, the target pixel extraction unit 31 may obtain the difference between the maximum value and the minimum value of the CT values in all the frame images corresponding to a single slice, and extract a pixel with the difference of a predetermined value (for example, 50 to 150).

The target pixel extraction unit 31 may execute one of the first extraction processing and the second extraction processing or both.

The target pixel extraction unit 31 may execute third extraction processing described below. For example, after the arrival time is determined through processing described later based on the target pixel obtained by the first and/or the second extraction processing, the target pixel extraction unit 31 may execute the third extraction processing to identify a pixel corresponding to the arrival time, determined in this manner, earlier than the arrival time 133 in the input function data. Then, the target pixel extraction unit 31 may exclude the pixel thus determined from the target pixels.

The target pixel extraction unit 31 may determine a position of the pixel thus extracted for each slice, as a position of the target pixel (an intra-organ pixel position) for which the output function is calculated.

The change-over-time determining unit 33 may determine the change-over-time in the CT value of the pixel at the target pixel position (intra-organ pixel position) based on the image data on the time-series CT images in a plurality of frames. For example, the change-over-time determining unit 33 may generate the TDC representing the change-over-time in the CT value at the target pixel position for each slice.

Figure 5B:
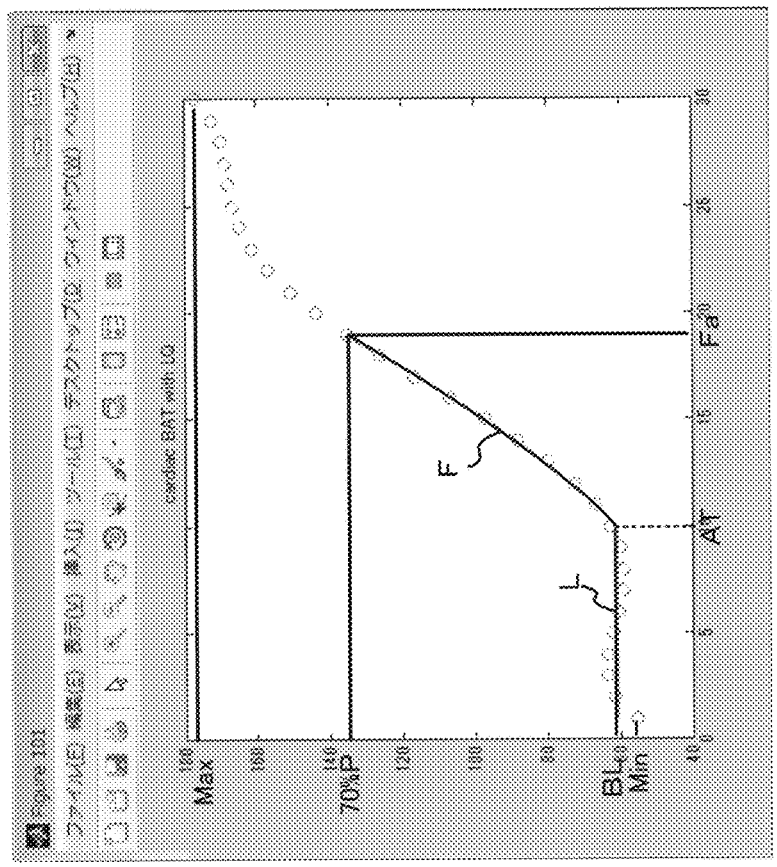
FIG. 5 is a diagram illustrating an example of a TDC of a CT value at a target pixel position.
Figure 5A:
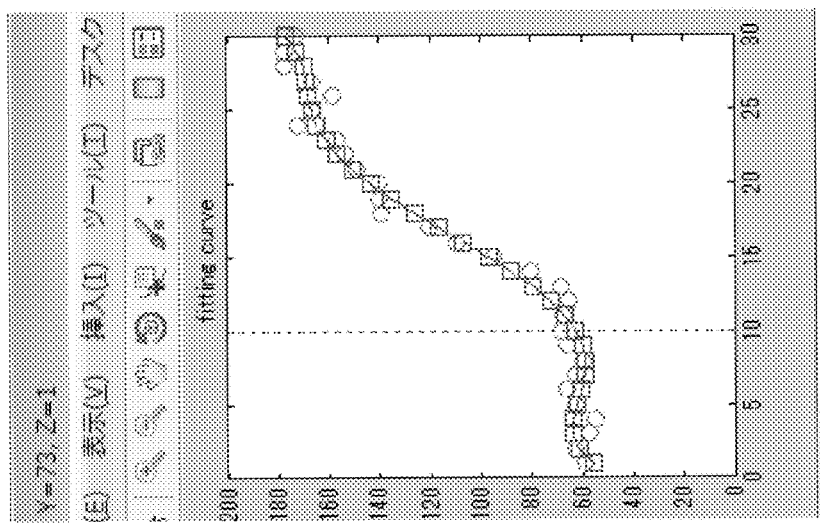

FIG. 5A illustrates an example of the TDC of the CT value at the target pixel position. In the figure, a point where a circle sign is plotted represents the CT value. The change-over-time determining unit 23 generates the TDC based on the ROI value, whereas the change-over-time determining unit 33 may generate the TDC by using the CT value.

The smoothing processing unit 35 may smooth the change-over-time determined by the change-over-time determining unit 33. The smoothing processing unit 35 may approximate the TDC with an mth-order function (m being a number equal to or larger than 3). For example, in the present embodiment, the smoothing processing unit 35 may approximate the TDC for each pixel generated by the change-over-time determining unit 33, to a fifth-order function with the least squares method. This is because the CT values (plotted with the circle signs) are largely dispersed as illustrated in FIG. 5A, and thus the TDC generated by the change-over-time determining unit 33 is less likely to be a smooth curve compared with the TDC generated by the change-over-time determining unit 23. Thus, the smoothing processing unit 35 may smooth the TDC by approximating the TDC to a higher-order function.

The smoothing processing unit 35 may approximate the TDC of the CT value with the mth-order function by performing the least squares method and the like. A curve on which squares in FIG. 5A are plotted represents the quintic function as a result of approximation by the smoothing processing unit 35, and each square represents a value sampled from the fifth-order function.

The TDC of the CT value may be smoothed by a method other than the fitting to the mth-order function described above. For example, the TDC may be generated with an average value involving peripheral pixels obtained and used, or the TDC may be smoothened with a moving average.

The function approximation processing unit 37 may determine an arrival time of the contrast medium for each pixel, based on the change-over-time in the CT value. The function approximation processing unit 37 may perform function approximation for the TDC smoothed by the smoothing processing unit 35 in a frame (time) direction for each pixel.

FIG. 5B is a diagram illustrating values sampled from the smoothed TDC. The function approximation processing unit 37 executes processing with an algorithm similar to that of the processing executed by the function approximation processing unit 25. The processing executed by the function approximation processing unit 37 is different from that executed by the function approximation processing unit 25 in the following point. More specifically, the function approximation processing unit 25 performs predetermined function approximation for the TDC based on the ROI value, whereas the function approximation processing unit 37 performs function approximation based for values sampled from the TDC (the approximated mth-order function) smoothed by the smoothing processing unit 35. The function approximation processing unit 37 may, in a manner similar to that of the function approximation processing unit 25, determine the upper limit frame and approximate the mth-order function before the upper limit frame with two straight lines and/or curved lines or with a plurality of functions, in order to determine the arrival time and the base value for each pixel.

The function approximation processing unit 37 may determine the arrival time and the base value for each pixel from the smoothed TDC for each pixel. More specifically, the function approximation processing unit 37 may determine the output function for each pixel.

The function approximation processing unit 37 may perform function approximation for a TDC that is not smoothed. In this case, the processing executed by the smoothing processing unit 35 may be omitted.

The output function data storage unit 15 stores therein data on the output function obtained by the output function obtaining unit 30. The output function data storage unit 15 may store therein the output function table 150.

FIG. 4B illustrates an example of a data structure of the output function table 150. For example, as illustrated in the figure, the output function table 150 includes a slice No 151, a pixel position 153, an arrival time 155, a base value 156, functions L and F 157, and a sampling value 159 as data items. The sampling value 159 corresponds to the ROI value 139 in the input function table 130. The sampling value 159 may be a value sampled from the smoothed TDC as a result of the function approximation processing executed by the function approximation processing unit 37. When the blood flow analysis processing unit 50 uses the output function for the blood flow analysis, the sampling value 159 or the functions L and F 157 may be corrected in such a manner that the arrival time 155 and the base value 156 are set to be at the origin, as in the case of the input function.

Referring to FIG. 1, the blood flow analysis processing unit 50 may perform the quantitative analysis for the blood flow rate in the heart based on the input function and the output function. For example, the blood flow analysis processing unit 50 executes predetermined analysis processing by referring to the input function table 130 and the output function table 150. Examples of the blood flow quantitative analysis method include a Patlak plot and deconvolution.

The result of the quantitative analysis performed by the blood flow analysis processing unit 50 may be displayed on the display device 5. For example, an image appropriately divided into a plurality of segments of a heart region may be displayed on the display device 5, with each segment displayed with a display mode corresponding to the blood flow rate in the segment. Alternatively, a 3D image of the heart based on the image data stored in the image data storage unit 11 may be displayed with each pixel in the 3D image displayed in accordance with the blood flow rate.

For example, the result of the quantitative analysis by the blood flow analysis processing unit 50 described above may be displayed side by side with the CT image or may be overlapped on the CT image. The coronary stenosis and the myocardium ischemia can be concurrently assessed through comparison between two images, in cases such as myocardium infraction or angina. The CT image may be displayed in a display mode corresponding to the difference in time between the arrival time for each pixel in the myocardium region and arrival time for the input function. The CT image may be displayed as a 3D image based on coordinate information on each pixel.

The difference in the arrival time between the input function and that at the heart muscle occurs because the input function is based on the change in the pixel value in the aorta region on the upstream side of the heart muscle. For example, the difference depends on the distance and the state of the blood flow path to each myocardium region. For example, a region near the apex cordis from which the blood flow path to the aorta is long involves a large difference in the arrival time. For example, a myocardium region as a destination of a blood flow path with a high resistance due to blocked blood vessel involves a large difference in the arrival time.

A procedure of processing executed by the image processing device 1 having the function described above is described below with reference to a flowchart.

Figure 6:
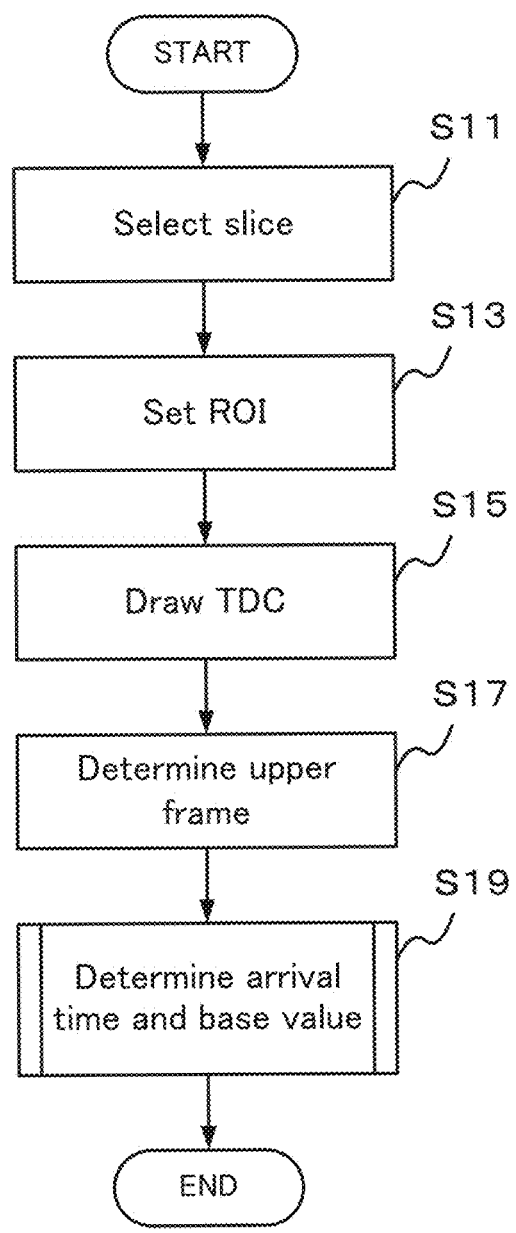
FIG. 6 is a flowchart illustrating an overall processing procedure of input function obtaining processing.

FIG. 6 is a flowchart illustrating an overall processing procedure of input function obtaining processing.

First of all, the input function obtaining unit 20 selects a slice image including an aorta region, and reads out image data on frame images corresponding to the slice from the image data storage unit 11 (S11). The slice may be selected automatically by the input function obtaining unit 20, or an analyst may check the automatically selected slice and then determine the slice after performing correction if required.

The ROI setting unit 21 sets a ROI in accordance with an operation of the analyst, while the display device 5 is displaying the frame image, in the slice image thus selected, in which the aorta region is clearly visible (S13).

When the ROI is set, the change-over-time determining unit 23 calculates the ROI values for all the frame images and draws the TDC based on the ROI values (S15).

The function approximation processing unit 25 determines the upper limit frame Fa defining the range of frames for which the input function is obtained, based on the TDC (S17). Then, the function approximation processing unit 25 determines the arrival time and the base value by performing function approximation processing on frames before the upper limit frame Fa (S19).

The processing of determining the arrival time and the base value is described in detail with reference to a flowchart.

Figure 7:
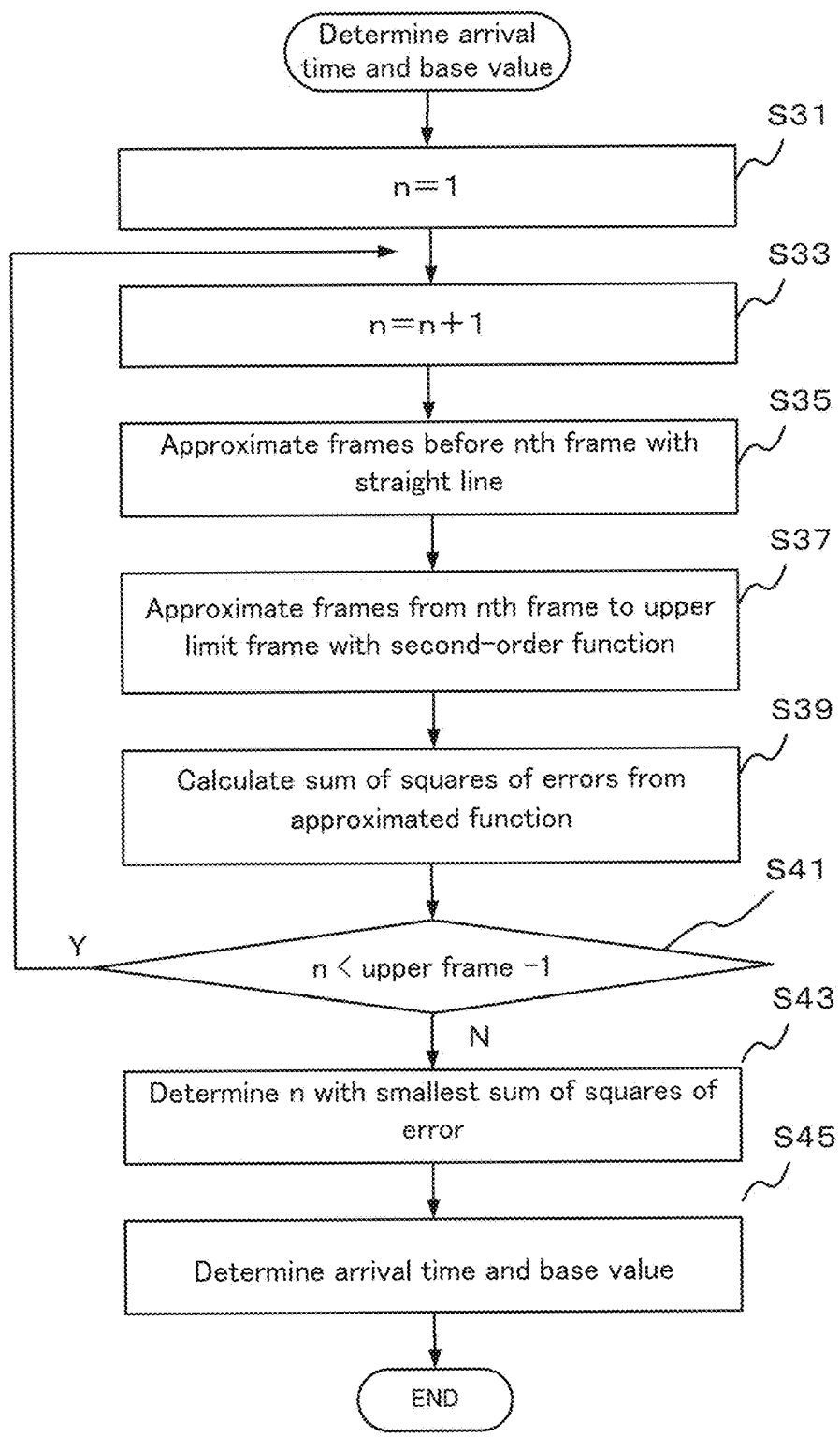
FIG. 7 is a flowchart illustrating a detailed procedure of processing of determining an arrival time and a base value.

FIG. 7 is a flowchart illustrating a detail procedure of the processing of determining the arrival time and the base value executed by the function approximation processing unit 25.

First of all, the function approximation processing unit 25 sets a variable n indicating the frame No to 1 (S31).

The function approximation processing unit 25 increments n by 1 (S33).

The function approximation processing unit 25 approximates the ROI values in frames before the nth frame to the single straight line L (S35).

The function approximation processing unit 25 approximates the ROI values in frames at and after the nth frame and at and before the upper limit frame to the second-order function F (S37).

The function approximation processing unit 25 calculates least square errors between the straight line L and the ROI values in the frames before the nth frame obtained by the processing described above. Similarly, the function approximation processing unit 25 calculates the least square errors between the second-order function F and the ROI values in the frames at and after the nth frame and at and before the upper limit frame to the second-order function F. Then, the function approximation processing unit 25 obtains the sum of the errors (S39).

The function approximation processing unit 25 repeats the processing from steps S53 to S59, until n reaches the upper limit frame −1 (S41).

When all the sums of the least square errors from n=2 to the upper limit frame −1 are obtained, the function approximation processing unit 25 determines n with the smallest sum of least square errors (S43).

The function approximation processing unit 25 determines the arrival time as the frame at the intersection between the straight line L and the second-order function F corresponding to n thus determined in step S63, and determines the corresponding ROI value as the base value. The base value may be the height of the straight line L (Y-intercept) (S45).

Thus, the arrival time and the base value as the input function are determined.

Figure 8:
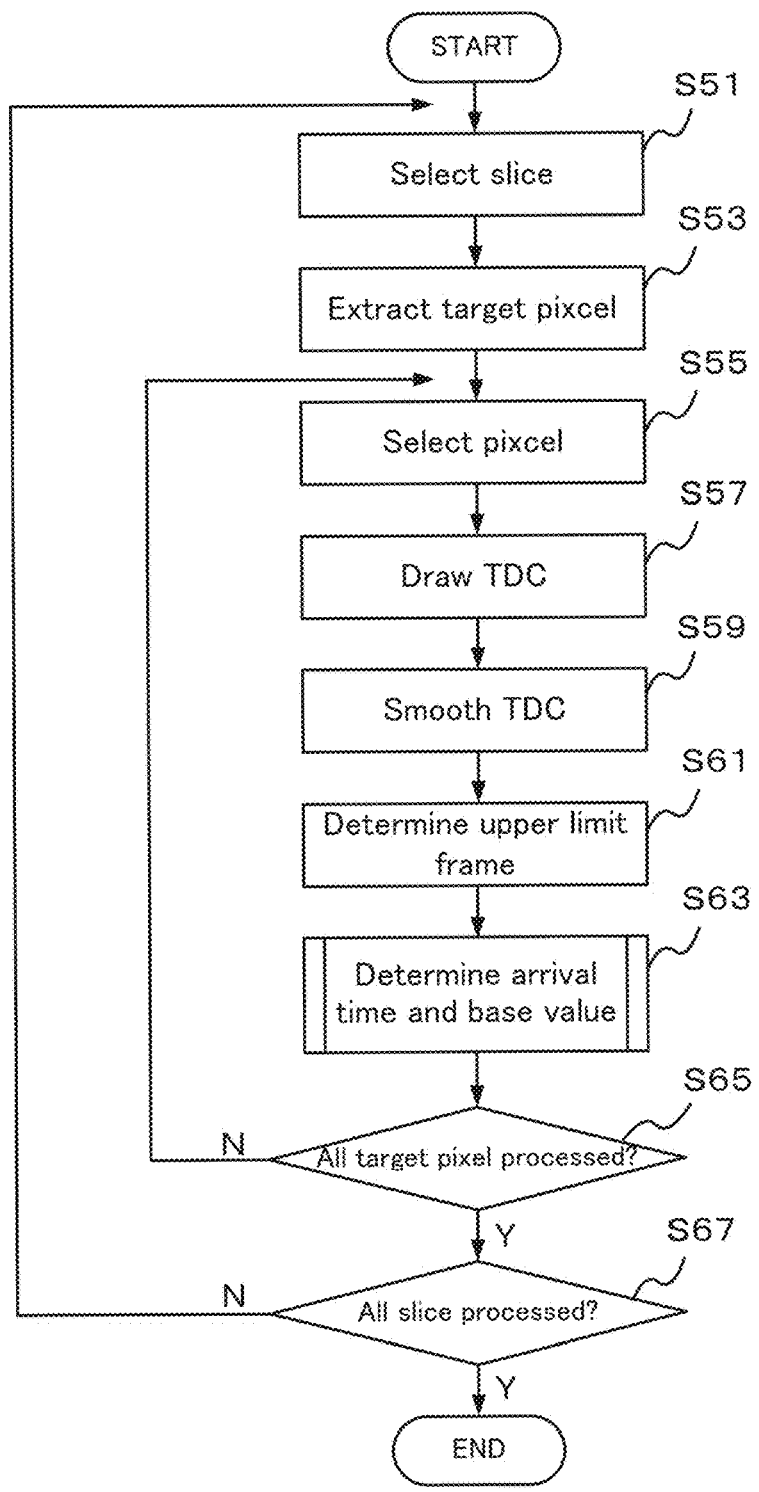
FIG. 8 is a flowchart illustrating an overall processing procedure of an output function obtaining processing.

FIG. 8 is a flowchart illustrating an overall processing procedure of output function obtaining processing.

First of all, the output function obtaining unit 30 selects a single slice image, and reads image data on frame images corresponding to the slice from the image data storage unit 11 (S51).

The target pixel extraction unit 31 regards, from among all the pixels in the slice selected, pixels, for which the CT values in all the frame images satisfy the condition described above, as the pixel in the heart region, and extracts the pixels as the target pixels (S53).

The change-over-time determining unit 33 selects one of the target pixels extracted in S53 (S55), and draws the TDC for the pixel thus selected (S57).

The smoothing processing unit 35 smooths the TDC drew in S57 through the fifth-order function approximation (S59). Then, the smoothing processing unit 35 determines on the basis of the smoothed TDC the upper limit frame Fa defining a range of frames for which the output function is obtained (S61). Then, the function approximation processing unit 37 executes function approximation processing on the frames before the upper limit frame Fa, and determines the arrival time and the base value (S63).

The output function obtaining unit 30 executes the processing from steps S55 top S63 on all the target pixels (S65).

The output function obtaining unit 30 executes the processing from steps S53 to S65 on all the slices (S67).

The detail of the function approximation processing for determining the arrival time and the base value in step S63 is the same as that in the flowchart illustrated in FIG. 7.

In this manner, the arrival time and the base value as the output function are determined.

The embodiment of the present invention is merely an example for describing the present invention, and there is no intension to limit the scope of the present invention to the embodiment. A person skilled in the art can implemented the present invention in various other modes without departing from the gist of the present invention.

REFERENCE SIGNS LIST

1 Image processing device
11 Image data storage unit
13 Input function data storage unit
15 Output function data storage unit
20 Input function obtaining unit
21 ROI setting unit
23 Change-over-time determining unit
25 Function approximation processing unit
30 Output function obtaining unit
31 Target pixel extraction unit
33 Change-over-time determining unit
35 Smoothing processing unit
37 Function approximation processing unit
50 Blood flow analysis processing unit

The invention claimed is:

1. An image processing device comprising:
a data storage unit that stores image data on time-series computed tomography (CT) images in a plurality of frames of an organ of a subject captured after a contrast medium has been administered; and
at least one processing unit that executes instructions to perform data processing activities to make determinations comprising:
an intra-organ pixel position, which is a position of a pixel in a region of the organ;
a change-over-time of a CT value of the pixel at the intra-organ pixel position, based on image data on the time series CT images in the plurality of frames; and
as an upper limit frame, a predetermined frame after a sharp rise in the CT value in the change-over-time, the predetermined frame being a frame before a frame from which a maximum value of the CT value or a first peak value of the CT value in the change-over-time is detected;
an arrival time at which the contrast medium has arrived at the organ at the intra-organ pixel position and a base value, which is a CT value serving as a base of the pixel at the intra-organ pixel position, based on the change-over-time before the upper limit frame.

2. The image processing device according to claim 1, the instructions further executable by the at least one processing unit to perform data processing activities to make determinations further comprising:
an approximate change-over-time before the upper limit frame with two or more functions,
wherein the arrival time and the base value are determined with the two or more functions.

3. The image processing device according to claim 1, the instructions further executable by the at least one processing unit to perform data processing activities to make determinations further comprising:
an approximate change-over-time before the upper limit frame with a normal cumulative distribution function or a cumulative distribution function,
wherein the arrival time and the base value are determined with the normal cumulative distribution function or cumulative distribution function.

4. The image processing device according to claim 2, wherein:
the determined change-over-time is approximated with an mth-order function (m being a number equal to or larger than three),
the upper limit frame is determined based on the mth-order function, and
the two or more functions include a linear and a quadratic function approximated to the mth-order function before the upper limit frame.

5. The image processing device according to claim 1, the instructions further executable by the at least one processing unit to perform data processing activities to make determinations further comprising:
a region of interest (ROI) setting including a plurality of pixels in a blood vessel region through which blood flows into the organ,
wherein the change-over-time in the CT value is a change-over-time in an ROI value determined based on a CT value of the pixel in the ROI,
wherein the arrival time is an arrival time at which the contrast medium has arrived at the blood vessel region determined based on a change-over-time in the ROI value, and
wherein the base value is determined based on the CT value of the pixel in the blood vessel region.

6. The image processing device according to claim 1, wherein a pixel with a CT value within a predetermined range is selected as the intra-organ pixel position in all the time-series CT images in the plurality of frames.

7. The image processing device according to claim 1, wherein the intra-organ pixel position is selected based on a difference between a maximum value and a minimum value of the CT value in the plurality of time-series CT images.

8. The image processing device according to claim 1, wherein
the organ is a heart, and
the times-series CT images in the plurality of frames are CT images captured in synchronization with an electrocardiogram.

9. The image processing device according to claim 2, wherein a pixel with a CT value within a predetermined range is selected as the intra-organ pixel position in all the time-series CT images in the plurality of frames.

10. The image processing device according to claim 2, wherein the intra-organ pixel position is selected based on a difference between a maximum value and a minimum value of the CT value in the plurality of time-series CT images.

11. The image processing device according to claim 2, wherein
the organ is a heart, and
the times-series CT images in the plurality of frames are CT images captured in synchronization with an electrocardiogram.

12. The image processing device according to claim 3, wherein a pixel with a CT value within a predetermined range is selected as the intra-organ pixel position in all the time-series CT images in the plurality of frames.

13. The image processing device according to claim 3, wherein the intra-organ pixel position is selected based on a difference between a maximum value and a minimum value of the CT value in the plurality of time-series CT images.

14. The image processing device according to claim 3, wherein
the organ is a heart, and
the times-series CT images in the plurality of frames are CT images captured in synchronization with an electrocardiogram.

15. An image processing method performed by an image processing device including a storage unit that stores therein image data on time-series computed tomography (CT) images in a plurality of frames, of an organ of a subject captured after a contrast medium has been administered, the image processing method comprising:
by the image processing device, determining an intra-organ pixel position, which is a position of a pixel in a region of the organ;
determining a change-over-time of a CT value of the pixel at the intra-organ pixel position, based on image data on the time series CT images in the plurality of frames;
determining, as an upper limit frame, a predetermined frame after a sharp rise in the CT value in the change-over-time, the predetermined frame being a frame before a frame from which a maximum value of the CT value or a first peak value of the CT value in the change-over-time is detected, and
determining an arrival time at which the contrast medium has arrived at an organ at the intra-organ pixel position and a base value, which is a CT value serving as a base of the pixel at the intra-organ pixel position, based on the change-over-time before the upper limit frame.

16. A method comprising:
storing image data of time-series computed tomography (CT) images in a plurality of frames of an organ of a subject captured after a contrast medium has been administered;
identifying an intra-organ pixel position which is a position of a pixel in a region of the organ;
calculating a change-over-time of a CT value of the pixel at the intra-organ pixel position based on image data on the time series CT images in the plurality of frames; and
determining, as an upper limit frame, a predetermined frame after a sharp rise in the CT value in the change-over-time, the predetermined frame being a frame before a frame from which a maximum value of the CT value or a first peak value of the CT value in the change-over-time is detected;
detecting an arrival time at which the contrast medium has arrived at the organ at the intra-organ pixel position and a base value, which is a CT value serving as a base of the pixel at the intra-organ pixel position, based on the change-over-time; and
outputting a data representation of at least the detected arrival time of the contrast medium.

* * * * *